(12) United States Patent
Seth et al.

(10) Patent No.: US 7,192,896 B2
(45) Date of Patent: Mar. 20, 2007

(54) DISPOSABLE CLEANING PRODUCT

(75) Inventors: Jayshree Seth, Woodbury, MN (US); Jerry W. Hall, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1116 days.

(21) Appl. No.: 10/001,158

(22) Filed: Nov. 15, 2001

(65) Prior Publication Data

US 2003/0100236 A1    May 29, 2003

(51) Int. Cl.
  *B32B 27/12* (2006.01)
(52) U.S. Cl. ..................... 442/400; 442/414
(58) Field of Classification Search ............... 442/400, 442/414
  See application file for complete search history.

(56) References Cited

U.S. PATENT DOCUMENTS

| | | | |
|---|---|---|---|
| 3,825,379 A | 7/1974 | Lohkamp et al. |
| 3,849,241 A | 11/1974 | Butin et al. |
| 3,929,678 A | 12/1975 | Laughlin et al. |
| 3,973,068 A | 8/1976 | Weber |
| 4,070,218 A | 1/1978 | Weber |
| 4,100,324 A | 7/1978 | Anderson et al. |
| RE31,885 E | 5/1985 | Meitner |
| 4,578,414 A | 3/1986 | Sawyer et al. |
| 4,933,229 A | 6/1990 | Insley et al. |
| 5,057,361 A | 10/1991 | Sayovitz et al. |
| 5,972,361 A | 10/1999 | Fowler et al. |
| 6,063,397 A | 5/2000 | Fowler et al. |
| 6,153,208 A | 11/2000 | McAtee et al. |
| 6,267,975 B1 | 7/2001 | Smith, III et al. |
| 6,338,855 B1 | 1/2002 | Albacarys et al. |

FOREIGN PATENT DOCUMENTS

WO    WO 98/52537    11/1998

(Continued)

OTHER PUBLICATIONS

Wente Van A., "Superfine Thermoplastic Fibers", *Industrial Engineering Chemistry*, vol. 48, p. 1342 et seq. (1956).

(Continued)

*Primary Examiner*—Elizabeth M. Cole
(74) *Attorney, Agent, or Firm*—William J. Bond

(57) ABSTRACT

The invention is directed at a disposable dry cleansing article that is formed from a melt extruded fibrous web that has incorporated into the fibers forming the web from 0.5 to 20 percent by weight of a melt extruded lathering surfactant. The invention, dry article generally comprises a melt extruded fibrous web of a thermoplastic polymer having a basis weight of from about 10 to 200 g/m², preferably 10 to 150 g/m² wherein the fibers have a lathering surfactant incorporated into the fiber at a level that allows the article to be used two (2) or more times with a rinse foam volume of 15 or more, with an initial foam volume of at least 50 ml.

The novel melt extruded web can be made by the following sequential steps: (a) providing to an extruder a thermoplastic resin, such as polypropylene; (b) blending into the resin a lathering surfactant at a temperature at which the surfactant is not significantly degraded; (c) forming the blend into melt extruded fibers, (d) collecting the fibers, (e) forming the fibers into a web and optionally, further treating the web by coating additional components, laminating to further layers or consolidating for strength or the like.

36 Claims, 1 Drawing Sheet

| | FOREIGN PATENT DOCUMENTS | |
|----|----------------|---------|
| WO | WO 99/13861 | 3/1999 |
| WO | WO 99/55303 | 11/1999 |
| WO | WO 01/45615 | 6/2001 |
| WO | WO 01/78672 | 10/2001 |
| WO | WO 02/092052 | 11/2002 |

OTHER PUBLICATIONS

Wente et al., "Manufacture of Superfine Organic Fibers", Report No. 4364 of the Naval Research Laboratories, published May 25, 1954.

DISPOSABLE CLEANING PRODUCT

BACKGROUND OF THE INVENTION

The invention concerns disposable dry cleansing articles formed from a melt extruded fibrous web that has incorporated into the fibers forming the web at a melt extruded lathering surfactant.

U.S. Pat. No. 4,578,414 describes wettable olefin polymer fibers. The fibers are formed from a composition comprising a polyolefin resin and one or more defined surface-active agents. Such agents may be present in an amount of from about 0.01 to about 5 percent by weight. The surface-active agents can be (1) an alkoxylated alkyl phenol in combination with a mixed mono-, di- and/or triglyceride; (2) or a polyoxyalkylene fatty acid ester; or (3) a combination of (2) with any part of (1). The preferred polyolefin is polyethylene, and all of the examples employed an ethylene/1-octene copolymer, the latter apparently being a minor component.

Disposable personal cleansing products have recently been proposed which use a lathering surfactant and optionally conditioners that are impregnated into a water insoluble substrate. This water insoluble substrate is typically a fibrous material such as a nonwoven fibrous web. An example of this execution is described in U.S. Pat. No. 6,063,397 which provides a combination of a lathering surfactant and a conditioner into a water insoluble substrate where the ratio of the surfactant to conditioner is less than 40:7. This product is dry as sold then wetted by the consumer and then disposed of after use. An earlier patent of the same genre proposes a lathering surfactant and an oil soluble conditioning agent at a ratio of less than 20:1, U.S. Pat. No. 5,972,361. This product is also dry as sold, wetted by the consumer and generally subsequently disposed of after a single use. U.S. Pat. No. 6,267,975 discloses a multilayer water insoluble substrate with the lathering surfactant and other ingredients located between the layers. The multiple layers have differing "Loft-Soft" ratios to enhance lathering. A wide variety of nonwoven type webs are described including air laid webs, meltblown webs, spunbond webs, carded webs and wet laid webs. In all these dry articles, the lathering surfactants are impregnated into the nonwoven web or the like by conventional coating techniques such as dip coating, slot coating or the like. Although effective for a single use, these coated webs however generally lose their effectiveness after a single use or rinsing.

Melt blown microfiber (BMF) webs are made by extruding a thermoplastic polymer or resin such as a polyolefin through a row of small, side-by-side orifices into a high velocity gaseous stream which attenuates the emerging resin into microfibers. The gaseous stream creates a turbulence which entangles the microfibers to form a coherent web that is deposited onto a collector such as a moving screen. It is known to make a BMF web hydrophilic by incorporating a surfactant into the web fiber by means of extruding a thermoplastic resin/surfactant premix. When the thermoplastic resin is polypropylene, an amount of surfactant exceeding 6% by weight of the resin may be required to maximize the hydrophilicity and absorbency properties of the web. More commonly, surfactant is topically applied, e.g., by being sprayed onto a finished BMF web, see U.S. Pat. Reissue No. 31,885 (Meitner) which concerns the use of BMF webs as articles or articles that can clean off both water and oil from a surface in a single pass.

U.S. Pat. No. 4,933,229 proposes a method to increase surfactant loading by use of a static mixer immediately prior to extruding the polymer. The resulting web has excellent wet web strength and is used as an absorbent article. The surfactant is not of the lathering type and the web is not usable as a cleansing article. In U.S. Pat. No. 4,578,414 (Sawyer et al.), the invention is characterized in that it "differs from the prior art by incorporating surface active agents directly into the bulk polymer resin rather than introducing a copolymer or applying a surface treatment to fabricated fibrous structures" (col. 6, 23–26). Sawyer goes on to say that preferred blends comprise about 95% to about 99.9% of the olefin polymer, the remainder being the surfactant.

U.S. Pat. No. 4,070,218 (Weber) concerns a spunbond nonwoven web which differs from a BMF web in that its fibers are substantially continuous and, as deposited, are substantially not fused together at crossing points. The Weber web is made from a mixture of a thermoplastic resin such as polypropylene and a surfactant (there called a "lubricating agent"). "Alternatively, the lubricating agent may be metered directly into extruder 12 if desired" (col. 2, 57–59). Then after being calendered, "the bonded web 34 is heated to cause the lubricating agent to migrate to the fiber surfaces" (col. 4). Weber's surfactant has a molecular weight in the range of from 200 to 4000.

There is a need for a disposable dry lathering cleansing article that is capable of multiple uses or rinsings, for example, for use in personal care or home care.

SUMMARY OF THE INVENTION

The invention provides a disposable dry cleansing article that is formed from a melt extruded fibrous web that has incorporated into the fibers forming the web from 0.5 to 20 percent by weight of a melt extruded lathering surfactant. The invention, dry article generally comprises a melt extruded fibrous web of a thermoplastic polymer having a basis weight of from about 10 to 200 $g/m^2$, preferably 10 to 150 $g/m^2$ wherein the fibers have a lathering surfactant incorporated into the fiber at a level that allows the article to be used two (2) or more times with a rinse foam volume of 5 or more, with an initial foam volume of at least 50 ml.

The novel melt extruded web can be made by the following sequential steps: (a) providing to an extruder a thermoplastic resin, such as polypropylene; (b) blending into the resin a lathering surfactant at a temperature at which the surfactant is not significantly degraded; (c) forming the blend into melt extruded fibers, (d) collecting the fibers, optionally directly as a web, and (e) forming a fibrous web and optionally, further treating the formed web by coating additional components, laminating to further layers or consolidating for strength or the like.

BRIEF DESCRIPTION OF THE DRAWINGS

The invention may be more easily understood in reference to the drawing in which.

DETAILED DESCRIPTION OF THE PREFERRED EMBODIMENT

Figure 1:
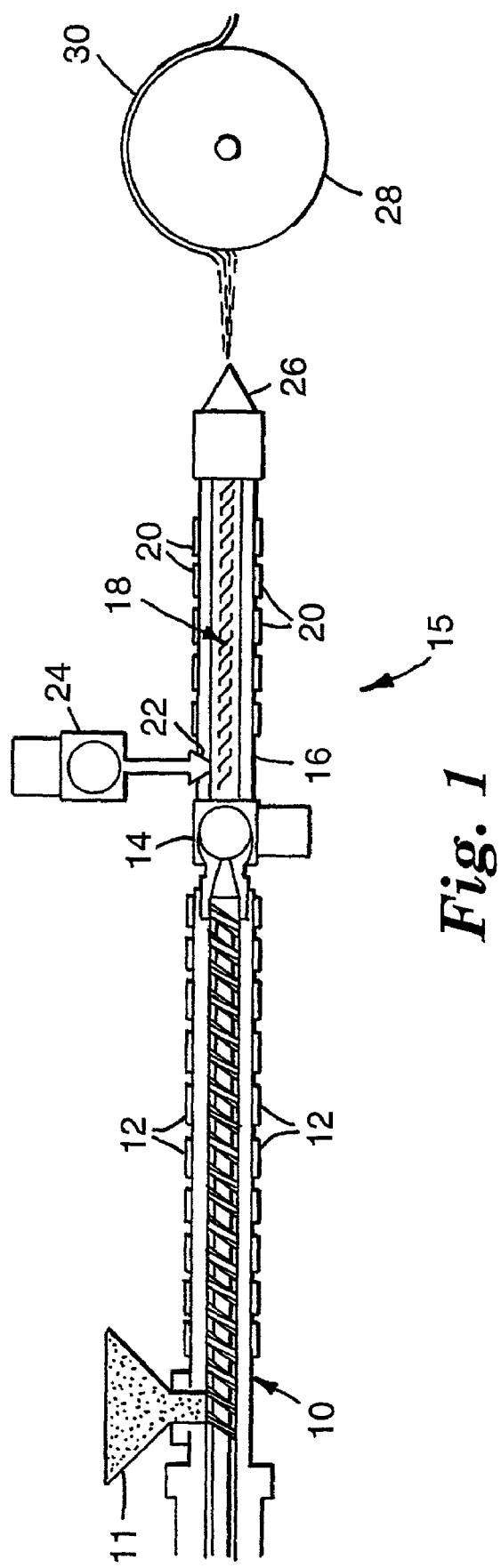
FIG. 1 is a schematic representation of apparatus for making a blown microfiber web for use in forming the present invention dry article product.

The nonwoven cleansing articles of the present invention are usable for cleansing the skin or hair. The fibers forming the nonwoven cleansing article are at least in part melt extruded fibers containing a lathering surfactant. These comprise melt extruded lathering surfactants. The articles can also contain conditioning and non-conditioning active or nonactive ingredients to be deposited onto the skin or hair. The skin conditioners and other ingredients, generally can be coated onto or impregnated into the substrate, where they are transferred directly to the skin or hair by surface contact of the wetted article to the skin. Additional lathering surfactants can also be dried onto or impregnated into the substrate.

The nonwoven cleansing article can have the same or differing textures on each side, e.g. a rough side and a smooth side. The nonwoven substrate can act as an efficient lathering and exfoliating implement. By physically coming into contact with the skin or hair, the cleansing article significantly aids in cleansing and removal of dirt, makeup, dead skin, and other debris. The nonwoven cleansing article can also be embossed to increase strength or optionally with a pattern to provide aesthetic properties.

A lathering surfactant is generally a surfactant which when incorporated into the fiber and used in the cleansing article and combined with water and mechanically agitated generates a foam or lather at an initial foam volume of greater than 30, preferably greater than 40 and most preferably 50 ml, as defined below. Preferably, these surfactants should be mild, which means that these surfactants provide sufficient cleansing benefits but do not overly dry the skin or hair (e.g., removing too much natural oil and/or moisture), and yet meet the lathering criteria described above. As incorporated into the melt extruded fibers, the melt extruded lathering surfactants should be capable of withstanding the temperature exposure encountered by the extrusion conditions. With more temperature resistant lathering surfactants, the surfactants can be blended with the resin prior to or within the extruder. With more temperature sensitive surfactants, or to increase surfactant levels, surfactants can be incorporated following the extruder in a mixer. Generally, the temperature sensitivity of the melt extruded lathering surfactants or other additional melt extruded active or inactive ingredients incorporated into the fibers can be determined by known techniques such as Differential Scanning Colorimetry (DSC) and/or Thermogravimetric Analysis (TGA). Other ingredients that do not degrade under typical extrusion temperatures include additional surfactants, active agents, fillers, processing aids, particulates, colorants, fragrance, conditioners, etc., which can also be added to the resin prior to, during or after (i.e., in a mixer) extrusion. Particulate or fibrous material can also be added into or onto the web subsequent to extrusion of the lathering surfactant containing melt extruded fibers by known techniques.

The term "limited use", is used herein to mean as article that is disposed or discarded after two or more uses, generally 3 to 10 uses, preferably 3 to 5 uses with a foam value where the foam value is generally at least 5 ml, preferably at least 10 ml, most preferably at least 15. The term "water-activated," as used herein, means that the present invention is presented to the end use consumer in dry form to be used after it is wetted with water. It is found that these articles produce a lather or are "activated" by contacting them with water and then further subjecting the article to mechanical forces, such as rubbing. The term "substantially dry," as used herein, means that prior to use, the article is substantially free of water and generally feels dry to the touch. Thus, the articles of the present invention will generally comprise less than about 10% by weight of water, preferably less than about 5% by weight of water, and more preferably less than about 1% by weight of water, the foregoing measured in a dry environment, e.g., low humidity. One of ordinary skill in the art would recognize that the water content of a article such as in the present invention can vary with the relative humidity of the environment. The term "mild" as used herein in reference to the lathering surfactants and articles of the present invention means that the articles of the present invention demonstrate skin mildness comparable to a mild alkyl glyceryl ether sulfonate (AGS) surfactant based synthetic bar, i.e. synbar.

In a further embodiment, the invention melt extruded article can be joined to other similar melt extruded article layers, other functionally different layers that can be such as those described in U.S. Pat. No. 6,153,208, the substance of which is incorporated by reference. These additional layers or webs can be paper webs manufactured by aqueous papermaking. The other layers could also include woven materials, or nonwoven materials (including air-laid, wet-laid, carded and hydroentangled nonwoven materials, as well as other melt extruded nonwovens such as spunbond or meltblown fibrous webs, foams, battings, and the like). Layers can be joined using any suitable method, including but not limited to adhesive bonding, mechanical bonding, thermal bonding, mechanical-thermal bonding, ultrasonic bonding, and combinations thereof. These additional can contain any of the active or nonactive ingredients mentioned herein or provide additional benefits such as absorbency, tensile properties, elasticity, abrasiveness or the like.

The articles of the present invention comprise one or more lathering surfactants which are incorporated into the melt extruded fibers forming the article. Preferred articles of the present invention comprise a sufficient amount of one or more lathering surfactants in the melt extruded fibers such that the articles are preferably capable of initially generating 50 ml of Foam Volume (medium hardness water at 95° C.) according to the Foam Volume Test described below. Preferably, the articles of the present invention comprise melt extruded fibers having from about 0.5% to about 20%, more preferably from about 1.0% to about 20%, and most preferably from about 5% to about 20%, based on the weight of the melt extruded fibers, of a melt extruded lathering surfactant.

A wide variety of lathering surfactants are useful herein and include those selected from the group consisting of anionic lathering surfactants, nonionic lather surfactants, amphotheric lathering surfactants, and mixtures thereof. Cationic surfactants can also be used as optional components, provided they do not negatively impact the overall lathering characteristics of the required, lathering surfactants.

Suitable additional surfactant materials for wetting out the nonwoven fibrous structures are anionic surfactants, such as aliphatic sulfates, for example, sodium dioctylsulfosuccinate (commercially sold as Aerosol-OT) or non-ionic surfactants such as polyethenoxy compounds, for example, nonylphenoxy poly(ethyleneoxy)ethanol (commercially solid as IGEPAL CO-730). Such a wetting surfactant can also be included in the polymer which is to be melt-processed, for example, as disclosed in U.S. Pat. Nos. 3,973,068 and 4,070,218.

Additional lathering surfactants can also be coated onto or impregnated into the nonwoven wipe article by known techniques. Such additional coated lathering surfactants would be in addition to those included within the melt extruded fibers. These additional lathering surfactants would not be limited by the degradation considerations of the melt extruded lathering surfactants. The additional lathering surfactants incorporated or impregnated physically within the wipe as a whole would be present at a weight percent of 0.5 to 20 based on the weight of the nonwoven wipe article or layer, preferably 1 to 15 percent. These additional coated lathering surfactants can enhance the initial latherability while allowing the melt extruded surfactant to be available for subsequent uses or rinsings.

Nonlimiting examples of lathering surfactants (either as melt additive and/or coated) which may be useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, all of which are incorporated by reference herein in their entirety.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates, and mixtures thereof. Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroy sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

The term "amphoteric lathering surfactant," as used herein, is also intended to encompass zwitterionic surfactants, which are well known to formulators skilled in the art as a subset of amphoteric surfactants. A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

The articles of the present invention can further comprise a conditioning component which is useful for providing a conditioning benefit to the skin or hair during the use of the article. This conditioning component would typically be coated or impregnated into the nonwoven wipe by conventional techniques such as disclosed in U.S. Pat. No. 6,063,397 or U.S. Pat. No. 6,269,975 the substance of which are incorporated by reference in their entirety. Alternatively, the conditioning component could be extruded with the melt extruded polymer. The conditioning component of the present invention can comprise: a water soluble conditioning agent; an oil soluble conditioning agent; a conditioning emulsion; or any combination or permutation of the three.

The weight ratio of the additional lathering surfactant coated onto or into the wipe to any conditioning component is generally less than about 40:7, preferably less than about 5:1, more preferably less than about 2.5:1, and more preferably less than about 1:1. Alternatively, the additional lathering surfactant comprises from about 1% to about 75%, preferably from about 10% to about 65%, and more preferably from about 15% to about 45%, by weight of the cleansing and conditioning component, and the conditioning component comprises from about 15% to about 99%, preferably from about 20% to about 75%, and more preferably from about 25% to about 55%, by weight of the cleansing and conditioning component.

The compositions which are added onto or impregnated into the articles of the present invention may comprise a wide range of additional optional ingredients. Some of these ingredients are listed in more detail herein. Particularly useful are added polymers (as distinct from the polymeric material which may form the substrate), various active ingredients, and cationic surfactants useful for delivering various non-conditioning or non-cleansing benefits of the skin or hair during the cleansing and conditioning process.

The articles of the present invention can optionally comprise a safe and effective amount of one or more active ingredients or pharmaceutically-acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically-acceptable salts of these active ingredients are useful herein.

Anti-acne actives include, but are not limited to, the keratolytics such as salicylic acid (o-hydroxybenzoic acid), derivatives of salicylic acid and resorcinol; retinoids and its derivatives; sulfur-containing D and L amino acids and their derivatives and salts; antibiotics and antimicrobials such as benzoyl peroxide, sebostats; and bile salts.

Anti-wrinkle and anti-skin atrophy actives include, but are not limited to, retinoic acid and its derivatives (e.g., cis and trans); retinol; retinal; retinyl esters; vitamin B3 compounds; salicylic acid and derivatives thereof; sulfur-containing D and L amino acids and their derivatives and salts, particularly the N-acetyl derivatives; thiols; hydroxy acids, phytic acid, lipoic acid; lysophosphatidic acid, and skin peel agents (e.g., phenol and the like).

Cosmetic soothing actives can be effective in preventing or treating inflammation of the skin. The soothing active enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Non-steroidal anti-inflammatory actives (NSAIDS) include the following categories: propionic acid derivatives; acetic acid derivatives; fenamic acid derivatives; biphenyl-carboxylic acid derivatives; and oxicams. All of these NSAIDS are fully described in U.S. Pat. No. 4,985,459 to Sunshine et al., issued Jan. 15, 1991, incorporated by reference herein in its entirety.

Topical anesthetic drugs useful or active agents include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; acetyl tyrosine; phospho-DOPA, brazilin; caffeine; coffee extracts; dihydroxyacetone; DNA fragments-, isobutyl methyl xanthine; methyl xanthine; Prostaglandins; tea extracts; theophyllinc; and mixtures thereof. Skin lightening actives can actually decrease the amount of melanin in the skin.

Sebum stimulators actives can increase the production of sebum by the sebaccous glands. These skin care actives are especially useful for post menopausal women who are sebum deficient. Nonlimiting examples of sebum stimulating actives include bryonolic acid, dehydroetiandrosterone (also known as DHEA), orizanol and mixtures thereof.

Sebum inhibitors actives can decrease the production of sebum by the sebaceous glands. Nonlimiting examples of sebum inhibiting actives include cucumber extracts, dehydroacetic acid and its salts, dichlorophenyl imidazoldioxolan, niacinamide, phloretin, S-carboxylmethyl cysteine, tioxolone, tocopherol, and mixtures thereof.

The articles of the present invention can also optionally comprise one or more cationic surfactants, provided these materials are selected so as not to interfere with the overall lathering characteristics of the required, lathering surfactants. Cationic surfactants are useful as anti-static agents or as emulsifiers. Nonlimiting examples of cationic surfactants useful herein include cationic alkyl ammonium salts, amino amides. Preferred cationic surfactants useful herein include those selected from the group consisting of dilauryl dimethy ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

The articles of the present invention can comprise a wide range of other optional components. These additional components should be pharmaceutically acceptable. The CTFA Cosmetic Ingredient Handbook, Second Edition, 1992 which is incorporated by reference herein in its entirety describes a wide variety of non-limiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anti-caking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, sunscreening agents, or aesthetic components such as fragrances, pigments, colorings, essential oils, skin sensates, astringents, skin soothing agents, and skin healing agents.

Melt extruded fibers suitable for forming the nonwoven fibrous layer or webs of the present invention nonwoven cleansing articles or wipes can be produced from a wide variety of thermoplastic polymers that are known to form fibers. Suitable thermoplastic polymers are selected from polyolefins, polyamides, polyesters, copolymers containing acrylic monomers, and blends and copolymers thereof. Suitable polyolefins include polyethylene, e.g., linear low density polyethylene, high density polyethylene, low density polyethylene and medium density polyethylene; polypropylene, e.g., isotactic polypropylene, syndiotactic polypropylene, blends thereof and blends of isotactic polypropylene and atactic polypropylene; and polybutylene, e.g., poly(1-butene) and poly(2-butene); polypentene, e.g., poly-4-methylpentene-1 and poly(2-pentene); as well as blends and copolymers thereof. Suitable polyamides include nylon 6, nylon 6/6, nylon 10, nylon 4/6, nylon 10/10, nylon 12, nylon 6/12, nylon 12/12, and hydrophilic polyamide copolymers such as copolymers of caprolactam and an alkylene oxide, e.g., ethylene oxide, and copolymers of hexamethylene adipamide and an alkylene oxide, as well as blends and copolymers thereof. Suitable polyesters include polyethylene terephthalate, polybutylene terephthalate, polycyclohexylenedimethylene terephthalate, and blends and copolymers thereof. Acrylic copolymers include ethylene acrylic acid, ethylene methacrylic acid, ethylene methylacrylate, ethylene ethylacrylate, ethylene butylacrylate and blends thereof. Particularly suitable polymers are polyolefins, including polyethylene, e.g., linear low density polyethylene, low density polyethylene, medium density polyethylene, high density polyethylene and blends thereof; polypropylene; polybutylene; and copolymers as well as blends thereof.

As used herein, the term "fiber" includes fibers of indefinite length (e.g., filaments or spunbond fibers) and fibers of discrete length, e.g., staple fibers or meltblown fibers. The extruded fibers used in connection with the present invention may be multicomponent fibers where one or more of the components can contain one or more lathsering surfactants. The term "multicomponent fiber" refers to a fiber having at least two distinct longitudinally coextensive structured polymer domains in the fiber cross-section, as opposed to blends where the domains tend to be dispersed, random, or unconstructed. The distinct domains may thus be formed of polymers from different polymer classes (e.g., nylon and polypropylene) or can be formed of polymers from the same polymer class (e.g., nylon) but which differ in their properties or characteristics. The term "multicomponent fiber" is thus intended to include, but is not limited to, concentric and eccentric sheath-core fiber structures, symmetric and asymmetric side-by-side fiber structures, island-in-sea fiber structures, pie wedge fiber structures, and hollow fibers of these configurations. Different polymers can be used to provide different properties or used as carriers for different melt additive components or additives.

Aqueous or hydrophilic active agents may be coated onto the nonwoven wipe, or incorporated into the fibers that form the cleansing article web, or introduced into the web as additive fibers which may be hydrophilic fibers or hydrophilically modified fibers. Hydrophilic fibers include natural or synthetic fibers such as cotton fibers, cellulosic fibers, rayon and the like. Cotton or other non-thermoplastic fibers, if used are preferably blended with thermoplastic fibers such that the nonwoven wipe has at least 50 percent thermoplastic fibers by weight, preferably 75 percent thermoplastic fibers. Further, any of a wide variety of surfactants, including ionic and nonionic surfactants, may be employed to hydrophilically modify the fibers. Suitable surfactants may be internal modifiers, i.e., the modifying compounds are added to the polymer composition prior to spinning or forming fibers, or topical modifiers, i.e., the modifying compounds are topically applied during or subsequent to the formation of fibers or nonwoven webs. An exemplary internal modification process is disclosed in U.S. Pat. No. 4,578,414 to Sawyer et al. An exemplary topical modification process is disclosed in U.S. Pat. No. 5,057,361 to Sayovitz et al. Illustrative examples of suitable surfactants include silicone based surfactants, e.g., polyalkylene-oxide modified polydimethyl siloxane; fluoroaliphatic surfactants, e.g., perfluoroalkyl polyalkylene oxides; and other surfactants, e.g., actyl-phenoxypolyethyoxy ethanol nonionic surfactants, alkylaryl polyether alcohols, and polyethylene oxides. Commercially available surfactants suitable for the present invention include various poly(ethylene oxide) based surfactants available under the tradename Triton, e.g., grade X-102, from Rohm and Haas Crop; various polyethylene glycol based surfactants available under the tradename Emerest, e.g., grades 2620 and 2650, from Emery Industries; various polyalkylene oxide modified polydimethylsiloxane based surfactants available under the tradename Silwet, e.g., grade Y12488, from OSI Specialty Chemicals; and alkenyl succinamide surfactants available under the tradename Lubrizol, e.g., grade OS85870, from Lubrizol Crop.; and polyoxyalkylene modified fluoroaliphatic surfactants available from Minnesota Mining and Manufacturing Co. The amount of surfactants required and the hydrophilicity of modified fibers for each application will vary depending on the type of surfactant selected and the type of polymer used. In general, the surfactant may be added, topically or internally, in the range of from about 0.1 to about 10%, desirably from about 0.3 percent to about 6%, by weight based on the weight of the fiber or the nonwoven web.

The additional active agents or additives can be impregnated by the user or preimpregnated into the nonwoven wipe by any conventional techniques useful for impregnating or applying liquid or powders on or into a porous material, such as spraying, dipping, coating and printing. Optionally, once the nonwoven article is impregnated with an active agent or other additive, the liquid content of any liquid containing active agent can be evaporated to provide a lower weight nonwoven pad that can be reactivated by subsequently applying an appropriate solvent or water.

The invention nonwoven fibrous article web can be directly formed from thermoplastic fiber forming polymers such as by spunbond or meltblown and like techniques that directly form nonwovens from a polymer melt. Alternatively, fibers can be extruded and subsequently formed into nonwoven webs by known techniques, such as carding, air layering, needle punching, wet laying and the like. These nonwovens fibrous webs can be modified by blending in additional discrete fibers or particulates, coated with additional ingredients, or include suitable melt additives for the intended end use.

The individual discrete cleansing articles can be of any suitable size, however, generally for most applications the wipes would have an overall surface area of from 10 to 100 $cm^2$, preferably from 20 to 50 $cm^2$ suitable for easy handling. As such, the articles are wipes that would be of a size suitable for insertion in a package, which could easily be placed in the user's purse or pocket. The material forming the dispensable containers is generally not of importance and can be formed of suitable papers, plastics, paper film laminates and the like. The shape of the wipes is generally rectangular; however, other suitable shapes such as oval, circular or the like can be used. Generally, the discrete wipes would be provided in a package containing multiple density articles or wipes, e.g., more than 2, preferably at least 10.

FIG. 1 illustrates one arrangement which is useful for making the a blown microfiber webs useful in forming the present invention dry cleansing article. The apparatus consists of a conventional BMF production configuration as taught, for example, in van Wente, "Superfine Thermoplastic Fibers," Industrial Engineering Chemistry, Vol. 48, pages 1342 et sec (1956), or in Report No. 4364 of the Naval Research Laboratories, published May 25, 1954 entitled "Manufacture of Superfine Organic Fibers" by van Wente, A., Boone, C. D., and Fluharty, E. L. The configuration consists of an extruder 10 having a resin hopper 11 and a series of heating jackets 12 which heat the extruder barrel. The molten polyolefin resin exits from the extruder barrel into a pump 14 which permits improved control over the flow of the molten polymer through the downstream components of the apparatus. Upon exiting from the pump 14, the molten resin flows into mixing means 15 including a resin conveying tube 16 which contains a Kenix type static mixer 18. A series of heating jackets 20 control the temperature of the molten resin as it passes through the conveying tube 16. The mixing means 15 also includes an injection port 22 near the inlet end of the conveying tube that is connected to a high pressure metering pump 24 which enables surfactant to be injected into the molten polyolefin resin stream as it enters the static mixer 18. After exiting from the conveying tube 16, the molten resin is delivered through a BMF die 26 into a high velocity hot air stream which draws out and attenuates the molten resin into microfibers. The microfibers solidify and form a cohesive web 30 as they travel to a collector 28. This method is particularly preferred in that it produces fine diameter fibers and can be directly formed into a web without the need for subsequent bonding processes. Further the chaotic fibrous stream produced by this method can easily incorporate discrete fibers or particles that are introduced into the fibrous stream prior to collection as a web, such as disclosed in U.S. Pat. No. 4,100,324. These added fibers or particles can become entangled in the fibrous matrix without the need for additional binders or bonding processes. These added fibers can be incorporated to add loft, abrasiveness or softness to the web. Where abrasiveness is desired, the added fibers are generally from 40 to 70 µm in diameter, whereas 1–30 µm diameter added fibers could be used where loft and/or softness is desired. The overall basis weight of this wipe product would generally be from 10 to 500 $g/m^2$.

The melt extruded fibers can also be formed by conventional spunbond techniques by adding the melt processable lathering surfactants, other surfactants and other melt processable additive components into the resin prior to extrusion. With spunbond webs however subsequent bonding is typically required and it is more difficult to incorporate additional discrete particles or fibers.

Test Methods

Basis Weight

A 10 cm by 10 cm sample was die cut from the webs and weighed to the nearest 0.1 gram. Three replicates were measured and averaged and reported as grams/meter$^2$.

Caliper

The thickness of the webs were measured in inches using a TMI direct contact gauge. Three measurements were taken and averaged and reported in millimeters.

Foam Volume

The ability of the webs to form a foam was determined by placing a 13 cm by 18 cm sample of the web in a 500 mL Erlenmeyer flask. The flask was then filled with 350 mL of 40° C. tap water and then sealed with a rubber stopper. The flask was shaken vigorously for 30 seconds after which the volume of the generated foam was measured by reading the increments marked on the side of the flask. The sample was then removed and the contents drained. This procedure was repeated until there was no more apparent foam. The test was truncated after five foamings. Maximum measurable foam volume was 200 mL.

COMPARATIVE EXAMPLES

C1: Olay Daily Facial Cleansing Cloth—Normal To Dry, Procter and Gamble Co.
C2: Noxema H2 Foam Cleansing Cloth, Procter and Gamble Co.
C3: Dove Daily Hydrating Cleansing Cloth—Sensitive Skin, Unilever Co.

Example 1

A blown microfiber web (BMF) was prepared using apparatus similar to that shown in FIG. 1 of the drawings and the method discussed in Wente, Van A., "Superfine Thermoplastic Fibers," in Industrial Engineering Chemistry, Vol. 48, pages 1342 et seq. (1956) or in Report No. 4364 of the Naval Research Laboratories, published May 25, 1954, entitled "Manufacture of Superfine Organic Fibers" by Wente, Van A., Boone, C. D., and Fluharty, E. L, and in U.S. Pat. Nos. 3,849,241 and 3,825,379, and in commonly assigned U.S. Pat. No. 4,933,229. The resin conveying tube 16 was 102 cm (40 in.) in length and had a 1.0 cm (⅜ in.) bore containing a 78.8 cm (31 inch) long Kenix type static mixing unit having 46 mixing elements, each element 1.7 cm (¹¹⁄₁₆ in.) in length. The injection port 22 was located 6.4 cm (2.5 in.) from the end of the resin conveying tube closest to the extruder. The conveying tube was equipped with heating jackets 20. A high pressure dual pump injection cart 24 equipped with two zenith pumps, was used to inject surfactant via the injection port 22 into the molten polyolefin stream as it enters the static mixer 18. After exiting from the conveying tube 16 the molten resin is delivered through a BMF die 26 into a high velocity hot air stream which draws out and attenuates the molten resin into microfibers. The microfibers solidy and form a cohesive web 30 as they travel to a collector 28. Generally, the fibers have an average diameter of less than 25 µm, preferably less than 10 µm.

A 1500 melt flow index polypropylene resin (Exxon "Escorene" 3746G, 90%) was tumble blended with a lathering surfactant (Taurinol I-78, sodium cocyl isethionate, Finetex, 10%) and then fed into a 38 mm (30:1 L/D) single screw Berlyn extruder 10, with a flat temperature profile of 200° C. A hydrophilic lathering surfactant blend consisting of a mixture of 70% glycerol monolaurate (Lauricidin from MedChem Labs) and 30% sorbitan monolaurate (Span 20 from Uniqema) maintained at approximately 71° C., was injected into the resin conveying tube 16 which was maintained at 200° C. The concentration of the hydrophilic surfactant blend was controlled by pump speed to 6% of the final extruded web weight. The polypropylene/surfactant blend was delivered to the die at a total rate of 1.14 kg/hr/cm (6.4 lb/hr/in). The temperature of the BMF die 26 was maintained at 230° C., the attenuating air was delivered to the die at a temperature of 230° C. and a flow rate of 160–175 standard cubic feet per minute. A 51 cm NRL (Navy Research Labs) die equipped with a die tip consisting of 0.43 mm diameter orifices spaced at 22 holes/cm was used. Blown microfibers were collected on a rotating drum placed 53.3 cm (21 in.) from the die outlet. The drum speed was adjusted to achieve a web basis weight of 60 grams/meter$^2$.

Example 2

To demonstrate a higher basis weight embodiment, a BMF web was prepared as in Example 1 except the collector drum speed was varied so as to produce a web having a final basis weight of 90 grams/meter$^2$. The final web had approximately 9.4% lathering surfactant and 6.0% hydrophilic surfactant incorporated in the microfibers.

Example 3

A BMF web was prepared as in Example 1 except no hydrophilic surfactants were added.

Example 4

To achieve a higher loading of lathering surfactant in the final web, a BMF web was prepared as in Example 1 except the polypropylene and lathering surfactant were precompounded in a twin screw extruder at a ratio of 85:15 and then pelletized prior to addition to a 40 mm (38:1 L/D) co-rotating Berstorff ZE twin screw extruder. A 51 cm DOD (Direct Orifice Drilled) die equipped with a die tip consisting of 0.38 mm diameter orifices spaced at 10 holes/cm was used. The final web had approximately 14.1% lathering surfactant and 6.0% hydrophilic surfactant incorporated in the microfibers.

Example 5

A lower basis weight embodiment was prepared as in Example 3 except the collector drum speed was varied so as to produce a web having a final basis weight of 30 grams/meter$^2$. A 40 mm (38:1 L/D) co-rotating Berstorff ZE twin screw extruder was used to deliver the polypropylene/lathering surfactant blend. No hydrophilic surfactants were used. A 51 cm DOD (Direct Orifice Drilled) die equipped with a die tip consisting of 0.38 mm diameter orifices spaced at 10 holes/cm was used. The final web had approximately 10.0% lathering surfactant and 0% hydrophilic surfactant incorporated in the microfibers.

Example 6

To demonstrate the addition of supplemental ingredients to the web, such as a processing aid, a BMF web was prepared as in Example 1 except 5% zinc stearate (Lubrazinc, Witco Chem.) was added to the hydrophilic surfactant blend in the pump injection cart. The final web had approximately 9.4% lathering surfactant and 6.0% hydrophilic surfactant incorporated in the microfibers.

Example 7

To demonstrate the addition of supplemental ingredients to the web, such as a conditioning component, a BMF web was prepared as in Example 1 except 5% mineral oil (Paddock Laboratories Inc.) was added to the hydrophilic surfactant blend in the pump injection cart. The final web had approximately 8.9% lathering surfactant and 6.0% hydrophilic surfactant incorporated in the microfibers.

Example 8

To demonstrate the use of a different lathering surfactant, a BMF web was produced as in Example 1 except Hostapur SAS93 (sodium C14-17 sec-alkylsulfonate, Clariant Corp.) was used as the lathering surfactant. A 40 mm (38:1 L/D) co-rotating Berstorff ZE twin screw extruder was used to deliver the polypropylene/lathering surfactant blend. A 51 cm DOD (Direct Orifice Drilled) die equipped with a die tip consisting of 0.38 mm diameter orifices spaced at 10 holes/cm was used. The final web had approximately 9.4% lathering surfactant and 6.0% hydrophilic surfactant incorporated in the microfibers.

Example 9

To demonstrate the ability to achieve higher loadings of lathering surfactant in the BMF web, a BMF web was prepared as in Example 1 except a blend of 50% Taurinol 78, 35% Lauricidin and 15% Span 20 was used in the pump injection cart. The collector drum speed was varied so as to produce a web having a final basis weight of 90 grams/meter$^2$. A 25 mm NRL (Navy Research Labs) die equipped with a die tip consisting of 0.43 mm diameter orifices spaced at 22 holes/cm was used. The final web had approximately 15.9% lathering surfactant and 7.4% hydrophilic surfactant incorporated in the microfibers.

Example 10

A BMF web was prepared as in Example 9 except the surfactant pump speed was reduced. The final web had approximately 13.4% lathering surfactant and 4.2% hydrophilic surfactant incorporated in the microfibers.

Example 11

A BMF web was prepared as in Example 9 except a blend of 50% Taurinol 78 and 50% Lauricidin was used in the pump injection cart. The final web had approximately 15.9% lathering surfactant and 7.4% hydrophilic surfactant incorporated in the microfibers.

Example 12

A BMF web was prepared as in Example 11 except the surfactant pump speed was reduced. The final web had approximately 13.4% lathering surfactant and 4.2% hydrophilic surfactant incorporated in the microfibers.

Example 13

A BMF web was prepared as in Example 12 except the surfactant pump speed was reduced. The final web had approximately 11.7% lathering surfactant and 2.2% hydrophilic surfactant incorporated in the microfibers.

Comparative Example C4

A BMF web was prepared as in Example 5 except no lathering or hydrophilic surfactants were used.

Comparative Example C5

A BMF web was prepared as in Example 5 except no lathering surfactants were used.

Comparative Example C6

The BMF web of Comparative Example C4 was then coated with a cleansing formulation containing 20% Velvetex BA-35 (cocoamidopropyl betaine, Henkel Corp.) and 80% water followed by oven drying at 66° C. The dry coating weight of the Velvetex BA-35 was 20 grams/meter$^2$.

Example 14

To demonstrate that the webs of the invention can be further coated with additional components, the BMF web of Example 5 was coated with a cleansing formulation containing 20% Velvetex BA-35 (cocoamidopropyl betaine, Henkel Corp.) and 80% water followed by oven drying at 66° C. The dry coating weight of the Velvetex BA-35 was 20 grams/meter$^2$.

Example 15

To demonstrate that the webs of the invention can be further coated with additional components, the BMF web of Example 4 was coated with a cleansing formulation containing 20% Velvetex BA-35 (cocoamidopropyl betaine, Henkel Corp.) and 80% water followed by oven drying at 66° C. The dry coating weight of the Velvetex BA-35 was 10 grams/meter$^2$.

Example 16

To demonstrate that webs of the invention could be made with multilayer coextruded fibers, the following procedure was used. Three layer BMF fibers were produced using an ABA three layer feedblock. A 40 mm (38:1 L/D) co-rotating Berstorff ZE twin screw extruder was used to deliver the A layers which consisted of 90% polypropylene resin (Escorene 3746G, Exxon Chem.) tumble blended with 10% of a lathering surfactant (Taurinol I-78, sodium cocoyl isethionate, Finetex). The B layer consisted of 100 percent polypropylene (Escorene 3746G) and was fed by a 38 mm (30:1 L/D) single screw Berlyn extruder. A 51 cm DOD (Direct Orifice Drilled) die equipped with a die tip consisting of 0.38 mm diameter orifices spaced at 10 holes/cm was used. The collector drum speed was varied so as to produce a web having a final basis weight of 60 grams/meter$^2$. The final web had approximately 6.7% lathering surfactant.

Example 17

To demonstrate that webs of the invention can be made with increased loft, the procedure of Example 16 was used except additional staple fibers (6 denier T295 polyester, KoSa) were introduced at a basis weight of 15 grams/meter², into the web via a secondary air stream as taught in U.S. Pat. No. 4,100,324. The final web had a basis weight of 75 grams/meter² and had approximately 5.4% lathering surfactant.

Example 18

To demonstrate that higher staple fiber loadings can be utilized, the web of Example 17 was produced except the T295 staple fibers were introduced at a basis weight of 30 grams/meter². The final web had a basis weight of 90 grams/meter² and had approximately 4.5% lathering surfactant incorporated in the microfibers.

Example 19

To demonstrate that higher staple fiber loadings can be utilized, the web of Example 17 was produced except the T295 staple fibers were introduced at a basis weight of 45 grams/meter². The final web had a basis weight of 115 grams/meter² and had approximately 3.5% lathering surfactant incorporated in the microfibers.

Example 20

To demonstrate that higher denier staple fibers can be utilized, the web of Example 17 was produced except 15 denier staple fibers (15d T295 polyester, KoSa) were introduced at a basis weight of 15 grams/meter². The final web had a basis weight of 75 grams/meter² and had approximately 5.4% lathering surfactant incorporated in the microfibers.

Example 21

To demonstrate that higher staple fiber loadings can be utilized, the web of Example 20 was produced except the T295 staple fibers were introduced at a basis weight of 30 grams/meter². The final web had a basis weight of 90 grams/meter² and had approximately 4.5% lathering surfactant incorporated in the microfibers.

Example 22

To demonstrate that higher staple fiber loadings can be utilized, the web of Example 20 was produced except the T295 staple fibers were introduced at a basis weight of 45 grams/meter². The final web had a basis weight of 115 grams/meter² and had approximately 3.5% lathering surfactant incorporated in the microfibers.

Example 23

To demonstrate the ability to achieve higher loadings of lathering surfactant in the BMF web in combination with additional staple fibers, a BMF web was prepared as in Example 1 except a blend of 50% Taurinol 78, 35% Lauricidin and 15% Span 20 was used in the pump injection cart. The collector drum speed was varied so as to produce a web having a final basis weight of 105 grams/meter². A 25 mm NRL (Navy Research Labs) die equipped with a die tip consisting of 0.43 mm diameter orifices spaced at 22 holes/cm was used. 6 denier T295 polyester staple fibers from KoSa were introduced at a basis weight of 15 grams/meter² into the web via a secondary air stream. The final web had approximately 13.6% lathering surfactant and 7.4% hydrophilic surfactant incorporated in the microfibers.

Example 24

To demonstrate that the webs of the invention can be laminated to additional substrates to provide for additional functionality, the web of Example 10 was thermally laminated to a 0.5 ounce/yard² spunbond polypropylene from PGI Nonwovens using a 5% point bonding roll at 88° C.

Example 25

To demonstrate that the webs of the invention can be embossed or calendered to provide for additional functionality or aesthetics, the web of Example 4 was embossed by running the web through a calendering nip consisting of a 5% point bonding roll at 88° C. and a smooth steel backup roll.

Table 1 below shows the ability of Examples 1–13 to generate significantly more lathering activity during repeated rinsings, as measured by foam volume, compared to three commercially available dry cleansing articles.

TABLE 1

| Example | 1st Rinse Foam Vol. (mL) | 2nd Rinse Foam Vol. (mL) | 3rd Rinse Foam Vol. (mL) | 4th Rinse Foam Vol. (mL) | 5th Rinse Foam Vol. (mL) |
|---|---|---|---|---|---|
| C1 | 200 | 45 | 0 | 0 | 0 |
| C2 | 190 | 0 | 0 | 0 | 0 |
| C3 | 200 | 23 | 0 | 0 | 0 |
| 1 | 78 | 45 | 33 | 23 | 13 |
| 2 | 145 | 55 | 30 | 18 | 13 |
| 3 | 80 | 38 | 15 | 5 | 0 |
| 4 | 200 | 48 | 35 | 30 | 15 |
| 5 | 85 | 15 | 13 | 5 | 0 |
| 6 | 68 | 48 | 13 | 5 | 0 |
| 7 | 115 | 30 | 5 | 0 | 0 |
| 8 | 75 | 58 | 53 | 25 | 15 |
| 9 | 200 | 58 | 35 | 20 | 18 |
| 10 | 200 | 40 | 30 | 13 | 5 |
| 11 | 200 | 44 | 30 | 20 | 15 |
| 12 | 200 | 50 | 15 | 5 | 0 |
| 13 | 200 | 70 | 50 | 25 | 20 |

Table 2 below shows the ability of post-coated Examples 14 and 15 to generate significantly more lathering activity during repeated rinsings, as measured by foam volume, compared to post-coated articles that do not have lathering surfactant incorporated directly into the fibers of the web.

TABLE 2

| Example | 1st Rinse Foam Vol. (mL) | 2nd Rinse Foam Vol. (mL) | 3rd Rinse Foam Vol. (mL) | 4th Rinse Foam Vol. (mL) | 5th Rinse Foam Vol. (mL) |
|---|---|---|---|---|---|
| C4 | 0 | 0 | 0 | 0 | 0 |
| C5 | 30 | 10 | 0 | 0 | 0 |
| C6 | 200 | 145 | 0 | 0 | 0 |
| 14 | 200 | 110 | 20 | 10 | 3 |
| 15 | 200 | 123 | 48 | 8 | 3 |

Table 3 below shows the ability to increase the loft or abrasiveness of the webs of the invention as measured by thickness, by adding staple fiber to the BMF webs.

TABLE 3

| Example | % Staple Fiber | Caliper (mm) |
| --- | --- | --- |
| 16 | 0 | 0.81 |
| 17 | 20 | 1.75 |
| 18 | 33 | 3.30 |
| 19 | 39 | 4.83 |
| 20 | 20 | 2.54 |
| 21 | 33 | 4.83 |
| 22 | 39 | 6.60 |
| 23 | 17 | 1.47 |

What is claimed is:

1. A disposable personal care cleansing article comprising a fibrous web containing melt extruded fibers, the melt extruded fibers comprising a blend of fiber-forming polymer with a melt extruded lathering surfactant, wherein the article has a foam volume for two or more rinsings, where the initial foam value is at least 30 ml and said article is substantially dry prior to use.

2. The cleansing article as defined in claim 1 wherein the foam volume is at least 5 ml for three or more rinsings.

3. The cleansing article as defined in claim 1 wherein the initial foam volume is 40 ml or more.

4. The cleansing article as defined in claim 1 wherein the initial foam volume is 50 ml or more.

5. The cleansing article as defined in claim 4 wherein the foam volume is at least 5 ml for three or more rinsings.

6. The cleansing article as defined in claim 1 wherein the melt extruded lathering surfactant is present in an amount of from 0.5 to 20 percent by weight of the melt extruded fibers containing lathering surfactant and the fibers further include a melt extruded hydrophilic surfactant.

7. The cleansing article as defined in claim 1 wherein the melt extruded lathering surfactant is present in an amount of from 5.0 to 20 percent by weight of the melt extruded fibers containing lathering surfactant.

8. The cleansing article as defined in claim 1 wherein the fiber-forming polymer consists of a polyolefin.

9. The cleansing article defined in claim 1 wherein an additional lathering surfactant is present in an amount of from 0.5 to 20% by weight of the cleansing article.

10. The cleansing article defined in claim 1 wherein the melt extruded lathering surfactant is present in an amount of from 5 to 20% by weight of the fiber forming polymer blend and the cleansing article has a foam volume of greater than 10 ml for three or more rinsings.

11. The cleansing article defined in claim 10 wherein at least one additional lathering surfactant is further added onto or impregnated into said cleansing article.

12. The cleansing article defined in claim 11 wherein said at least one additional lathering surfactant comprises from about 0.5% to about 20 percent by weight of the cleansing article.

13. The cleansing article defined in claim 12 wherein said lathering surfactant is selected from the group consisting of anionic lathering surfactants, nonionic lathering surfactants, amphoteric lathering surfactants, and mixtures thereof.

14. The cleansing article defined in claim 13 wherein said anionic lathering surfactant is selected from the group consisting of sarcosinates, sulfates, isethionates, phosphates, taurates, lactylates, glutamates and mixtures thereof; wherein said nonionic lathering surfactant is selected from the group consisting of amine oxides, alkyl glucosides, alkyl polyglucosides, polyhydroxy fatty acid amides, alkoxylated fatty acid esters, sucrose esters, and mixtures thereof; and wherein said amphoteric lathering surfactant is selected from the group consisting of betaines, sultaines, hydroxysultaines, alkyhminoacetates, iminodialkanoates, aminoalkanoates, and mixtures thereof.

15. The cleansing article defined in claim 1 wherein the melt extruded surfactant is sodium cocoyl isethionate.

16. The cleansing article defined in claim 13 further comprising a conditioning component.

17. The cleansing article defined in claim 13 wherein said article further comprises a safe and effective amount of one or more active ingredients selected from the group consisting of anti-acne actives, anti-wrinkle and anti-skin atrophy actives skin barrier repair actives, non-steroidal cosmetic soothing actives, non-stearoidal anti-inflammatory actives, topical anesthetics, artificial tanning agents and accelerators, skin lightening actives, sebum stimulators, sebum inhibitors, anti-microbial and anti-fungal agents, sunscreen actives, anti-oxidants, and mixtures thereof.

18. The cleansing article defined in claim 1 wherein said the fibrous web comprises a meltblown fiber web.

19. The cleansing article defined in claim 18 wherein the melt extruded fibers are polyolefin fibers.

20. The cleansing article defined in claim 19 wherein the melt extruded fibers contain from 0.5 to 20% by weight a melt extruded lathering surfactant.

21. The cleansing article defined in claim 19 wherein the melt extruded lathering surfactant comprises sodium cocoyl isethionate.

22. The cleansing article defined in claim 19 wherein the melt extruded fiber webs further has incorporated within its structure additional discrete fibers or particles.

23. The cleansing article defined in claim 1 wherein the cleansing article has a basis weight of from 10 to 200 $g/m^2$.

24. The cleansing article defined in claim 19 wherein the melt extruded fibers are multicomponent fibers.

25. The cleansing article defined in claim 1 wherein the melt extruded fibers are multicomponent fibers.

26. The cleansing article defined in claim 1 wherein an additional layer is joined to the melt extruded fiber containing layer.

27. The cleansing article defined in claim 26 wherein the additional layer is a functionally different layer.

28. The cleansing article defined in claim 1 wherein the melt extruded fibers are a continuous fiber.

29. The cleansing article defined in claim 1 wherein the melt extruded fibers are a discontinuous fiber.

30. The cleansing article defined in claim 18 wherein the melt extruded fibers are a multicomponent fiber.

31. The cleansing article defined in claim 19 wherein the cleansing article nonwoven fibrous web has a basis weight of from 10 to 100 $g/m^2$.

32. The cleansing article defined in claim 1 wherein the cleansing article is from 10 to 100 $cm^2$ and is provided in a package containing more than 2 cleansing articles.

33. The cleansing article defined in claim 32 wherein the package contains at least 10 cleansing articles.

34. The cleansing article defined in claim 16 wherein said conditioning component is melt extruded.

35. The cleansing article defined in claim 1 wherein the cleansing article is embossed with a pattern.

36. The cleansing article defined in claim 1 wherein the melt extruded fibers further include a hydrophilic surfactant.

* * * * *